United States Patent
Muramatsu et al.

(10) Patent No.: US 8,628,600 B2
(45) Date of Patent: Jan. 14, 2014

(54) METHOD FOR EXTRACTING HEXAVALENT CHROMIUM IN A POLYMER MATERIAL

(75) Inventors: Miho Muramatsu, Kanagawa (JP); Mitsuhiro Oki, Kanagawa (JP); Miyuki Takenaka, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 13/346,259

(22) Filed: Jan. 9, 2012

(65) Prior Publication Data
US 2012/0137830 A1    Jun. 7, 2012

Related U.S. Application Data

(63) Continuation of application No. PCT/JP2009/003167, filed on Jul. 7, 2009.

(51) Int. Cl.
    *C22B 3/00*    (2006.01)
(52) U.S. Cl.
    USPC .............................................. 75/721; 423/53
(58) Field of Classification Search
    USPC .......................................................... 75/721
    See application file for complete search history.

(56) References Cited

U.S. PATENT DOCUMENTS

| | | | |
|---|---|---|---|
| 5,801,204 A | 9/1998 | Johansson et al. | 521/41 |
| 6,881,303 B2 * | 4/2005 | Inoue et al. | 201/2.5 |
| 2007/0048873 A1 | 3/2007 | Tachibe et al. | |

FOREIGN PATENT DOCUMENTS

| | | |
|---|---|---|
| JP | 2003-172696 | 6/2003 |
| JP | 2006-132979 | 5/2006 |
| JP | 2007-064862 | 3/2007 |
| JP | 2008-076348 | 4/2008 |
| JP | 2008-157865 | 7/2008 |
| JP | 2008-232748 | 10/2008 |

OTHER PUBLICATIONS

Ichikawa et al. Machine translation of JP 2008232748 A. Oct. 2, 2008.
Online information of melting point and boiling point of Oleic acid, CAS 112-80-1_Oleic acid, Jul. 2012.
International Search Report issued Sep. 15, 2009 in PCT/JP2009/003167 filed Jul. 7, 2009.
Tokuzo Kanbe, et al.; "Chromate conversion coatings on electroplated zinc and cadmium coatings"; JIS H8625, 1993, pp. 1-12.
"Alkaline Digestion for Hexavalent Chromium"; EPA Method 3060A, SW-846, Dec. 1996, pp. 3060A-1~3060A-15.
Office Action issued Sep. 2, 2013, in corresponding Japanese Patent Application No. 2011-521706 (with attached English Translation).

* cited by examiner

*Primary Examiner* — Jie Yang
*Assistant Examiner* — Xiaowei Su
(74) *Attorney, Agent, or Firm* — Oblon, Spivak, McClelland, Maier & Neustadt, L.L.P.

(57) ABSTRACT

One embodiment of method for extracting hexavalent chromium includes preparing a liquid sample by adding a fatty acid to a polymer material, adding water or an aqueous alkali solution to this sample, and extracting hexavalent chromium contained in the sample in the water or the aqueous alkali solution.

16 Claims, 1 Drawing Sheet

METHOD FOR EXTRACTING HEXAVALENT CHROMIUM IN A POLYMER MATERIAL

CROSS-REFERENCE TO RELATED APPLICATION

This application is continuation application based upon the International Application PCT/JP2009/003167, the International Filing Date of which is Jul. 7, 2009, the entire content of which is incorporated herein by reference.

FIELD

Embodiments relates to a method for extracting hexavalent chromium contained in a polymer material.

BACKGROUND

In recent years, the trend to eliminate the use of hazardous materials is becoming increasingly stringent, out of concerns about environmental problems. For example, restrictions such as "Restriction on Hazardous Substances (RoHS)" are implemented in Europe. According to this restriction, it is demanded to guarantee that specific hazardous substances are not contained in the material and components of a product. Among the substances restricted in Europe, chromium is demanded to be under different management depending on the valency, and only hexavalent chromium in products is defined as an object of restriction. However, since chromium has a nature that the valency is changed by an oxidation-reduction reaction, there is a demand for a pretreatment method for extracting recovering only hexavalent chromium with high yield, without changing its valency.

In the case of the water-soluble hexavalent chromium compound in a polymer, JP-A 2006-132979(KOKAI) discloses that hexavalent chromium dissolve into the organic acid salt from the pulverized polymer using supersonic wave.

Furthermore, JP-A 2008-232748 (KOKAI) suggests another method. When a polymer that dissolve in water-soluble organic solutions, it dissolve into a water-soluble organic solution then adding an aqueous alkali solution to it. Thus, hexavalent chromium is extracted by dissolving in aqueous alkali solution.

DETAILED DESCRIPTION

Figure 1:
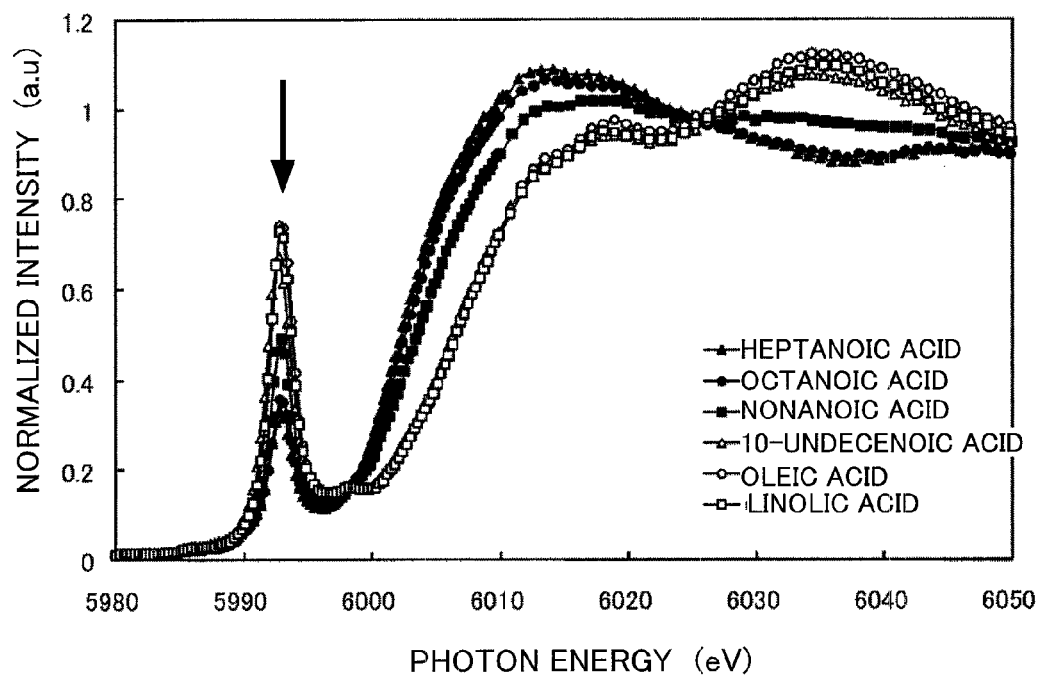
FIG. 1 is a diagram showing the XANES analysis results after the dissolution of a polymer material in a fatty acid.

The method for extracting hexavalent chromium contained in a polymer material of the present embodiment includes preparing a liquid sample by adding a fatty acid to a polymer material, adding water or an aqueous alkali solution to this sample, and dissolving extracting hexavalent chromium contained in the sample in the water or the aqueous alkali solution.

Specifically, first, a polymer material to be used as an object of extraction of hexavalent chromium is provided. The polymer material is, for example, a polyethylene (PE) resin or a polypropylene (PP) resin. It has been found by the inventors that a polyethylene (PE) resin and a polypropylene (PP) resin, which are both indissoluble resins, are dissolved in fatty acids.

Subsequently, the polymer material is subjected to a pulverization treatment to finely divide the material. When the polymer material is subjected to a pulverization treatment, the polymer material can be easily dissolved in fatty acids.

Subsequently, a fatty acid is added to the pulverization-treated polymer material, and thereby a liquid sample is prepared. Here, it is desirable that the polymer material become a uniform liquid sample when a fatty acid is added. The form of the uniform liquid sample may be dissolution or may be swelling. Hereinafter, the form of the uniform liquid sample will be referred to as dissolution, but according to the present specification, the form is defined to include the concept of swelling as well.

Table 1 illustrates examples of the fatty acid used in the dissolution of the polymer material, and the respective carbon numbers, melting points, and boiling points of the fatty acids are presented.

TABLE 1

| Fatty acid | Carbon number | Melting point (° C.) | Boiling point (° C.) |
|---|---|---|---|
| Hexanoic acid | 6 | −3 | 205 |
| Heptanoic acid | 7 | −7.5 | 223 |
| Octanoic acid | 8 | 15-17 | 233-241 |
| Nonanoic acid | 9 | 11-13 | 247-259 |
| Decanoic acid | 10 | 31 | 270 |
| 10-Undecenoic acid | 11 | 24.5 | 275 |
| Oleic acid | 18 | 16 | 203-205 (@5 mmHg) |
| Linoleic acid | 18 | −5 | 229-230 (@16 mmHg) |
| α-Linolenic acid | 18 | −11.3 | 137 (@0.07 mmHg) |

Here, the fatty acid used in the dissolution of the polymer material is preferably a fatty acid having a melting point of 30° C. or lower and a boiling point of 200° C. or more. If the melting point is 30° C. or lower, since the fatty acid is liquid at room temperature, workability is enhanced, and the operation of extraction is made easy. Furthermore, if the boiling point is 200° C. or higher, it is made possible to perform dissolution in a temperature range in which the polymer material is softened, and the time of dissolving the resin can be shortened.

Here, at the time of preparing the liquid sample, when the liquid sample is heated and stirred, the time required for the preparation of a uniform liquid sample can be shortened. The heating temperature is preferably 300° C. or lower. If the heating temperature is higher than 300° C., there is a risk that the fatty acid itself may be decomposed.

When the polymer material is dissolved in a fatty acid, there is a risk that hexavalent chromium may be reduced and turn into trivalent chromium. FIG. 1 is a diagram showing the XANES (X-ray Absorption Near Edge Structure) analysis results obtained after the dissolution of the polymer material in a fatty acid. The results are analysis results obtained when a polymer material containing hexavalent chromium is dissolved in various fatty acids having different carbon numbers and heated to 170° C. or higher. The vertical axis exhibits normalized intensity in order to relatively compare the amounts of change from hexavalent chromium to trivalent chromium in the respective fatty acids.

As is obvious from FIG. 1, the height of the pre-edge peak characteristic to hexavalent chromium, which is indicated by an arrow in the diagram, is such that in the case of a fatty acid having a carbon number of 9 or less, that is, in the case of heptanoic acid, octanoic acid or nonanoic acid, the height is very low as compared with the case of a fatty acid having a carbon number of 11 or greater, that is, 10-undecenoic acid, oleic acid or linoleic acid. This is because a fatty acid having a carbon number of 9 or less has higher acidity compared with a fatty acid having a carbon number of 11 or greater, and therefore, the reduction reaction of hexavalent chromium is accelerated, causing an increase in the amount of change to trivalent chromium.

Therefore, a fatty acid having a carbon number of 11 or greater is preferred from the viewpoint of suppressing the change of valency from hexavalent chromium to trivalent chromium. Particularly, at the time of preparing a sample, when the sample is heated and stirred, the reduction reaction proceeds easily. Thus, a fatty acid having a carbon number of 11 or greater is preferred.

Next, water or an aqueous alkali solution is added to this liquid sample, and the hexavalent chromium contained in the sample is dissolved in the water or the aqueous alkali solution. If the hexavalent chromium contained in the polymer material is a compound which dissolves only in an aqueous alkali solution, such as lead chromate or zinc chromate, an aqueous alkali solution is used. Furthermore, if the hexavalent chromium contained in the polymer material is a water-soluble, compound such as potassium dichromate or sodium dichromate, water or an aqueous alkali solution is used.

The aqueous alkali solution used is, for example, aqueous solution of LiOH, NaOH, or KOH. The concentration of the aqueous alkali solution is preferably equal to or higher than 0.1 mol/L and equal to or lower than 1.0 mol/L. If the concentration is lower than 0.1 mol/L, dissolution of hexavalent chromium in the aqueous alkali solution does not proceed, and there is a risk that the recovery of hexavalent chromium may be insufficient. Furthermore, if the concentration is higher than 1.0 mol/L, there is a risk that the fatty acid and the aqueous alkali solution react with each other, and the solution may be solidified.

Next, separation of the solution dissolving hexavalent chromium into an oil layer and an aqueous layer is carried out. This separation is carried out using, for example, a centrifuge or a separating funnel. A quantitative analysis of hexavalent chromium can be carried out using the solution of the separated aqueous layer portion.

In order to increase the recovery of hexavalent chromium, if necessary, it is also acceptable to prepare a solution by further adding water or an aqueous alkali solution to the separated oil layer, and to repeat the separation of an oil layer and an aqueous layer.

The solution obtained according to the method for extracting hexavalent chromium of the present embodiment is, for example, subjected to a quantitative analysis of hexavalent chromium. The quantitative analysis is carried out by, for example, diphenylcarbazide absorption photometry according to the specification of JIS H8625. Meanwhile, the method of the quantitative analysis of hexavalent chromium is not limited to diphenylcarbazide absorption photometry, and may also be carried out by methods such as ion chromatography, or an ICP emission spectrometric method.

According to the present embodiment, hexavalent chromium can be conveniently extracted from a polymer material with a high recovery.

While certain embodiments have been described, these embodiments have been presented by way of example only, and are not intended to limit the scope of the inventions. Indeed, method for extracting hexavalent chromium described herein may be embodied in a variety of other forms; furthermore, various omissions, substitutions and changes in the form of the devices and methods described herein may be made without departing from the spirit of the inventions. The accompanying claims and their equivalents are intended to cover such forms or modifications as would fall within the scope and spirit of the inventions.

For example, in regard to the polymer material which is the extraction object of hexavalent chromium, a polyethylene (PE) resin and a polypropylene (PP) resin are illustrated. The present invention is particularly useful because, the present invention uses fatty acids for the polyethylene (PE) resin and the polypropylene (PP) resin, which are indissoluble resins for which solvents appropriate for the extraction of hexavalent chromium could not be found hitherto. However, the polymer material to be used as an object of extraction is not intended to be limited to these PE resin and PP resin.

In addition to that, all methods for extracting hexavalent chromium, which include the elements of the present invention and can be subjected to appropriate modification of design by a person having ordinary skill in the art, are included in the scope of the present invention. The scope of the present invention will be defined by the scope defined by the claims and equivalents thereof.

EXAMPLES

Hereinafter, the method for extracting hexavalent chromium and the method for quantitative analysis will be specifically explained by way of Examples. However, the present invention is not intended to be limited to the matter described in the Examples.

Examples 1 to 6

0.1 g of a lead chromate-containing PE resin powder which contained 1% by mass of hexavalent chromium was weighed. 10 mL of each fatty acid was added to this powder, and the mixture was covered with a watch glass as a lid. A hot stirrer was set at 250° C. and at a speed of magnetic rotation of 500 rpm, and the mixture was heated and stirred from room temperature by the hot stirrer. When it was confirmed that the resin reached a uniform liquid state (solution temperature: about 180° C.) in the fatty acid by swelling or dissolution, the set temperature of the hot plate was lowered to 110° C. This liquid sample (solution) maintained fluidity even when the temperature decreased.

To the liquid sample with its temperature lowered to about 90° C., 10 mL of each aqueous alkali solution at a concentration of 0.25 mol/L was added, and the resulting mixture was heated and stirred for 15 minutes to 30 minutes at a hot plate temperature of about 110° C. (solution temperature: 60° C. to 90° C.). After the heating and stirring, the liquid was transferred to a centrifuge tube, and was subjected to centrifugation for 5 minutes at 5000 rpm to separate an aqueous layer and an oil layer. For the oil layer, the operation of further adding the aqueous alkali solution and centrifuging was repeated. The extraction of hexavalent chromium by means of the addition of the aqueous alkali solution and the separation of an aqueous layer and an oil layer, was carried out for 5 times in total.

The aqueous layer obtained by the 5 times of extraction was used to quantitatively measure the concentration of hexavalent chromium by diphenylcarbazide absorption spectrophotometry. The recovery of hexavalent chromium was calculated from the content of hexavalent chromium in the PE resin powder and the quantitative measurement results. The results are presented in Table 2.

TABLE 2

|  | Organic fatty acid | Aqueous alkali solution | Number of extraction operations (times) | Recovery (%) |
|---|---|---|---|---|
| Example 1 | Linolic acid | LiOH | 5 | 73.0 |
| Example 2 | Linolic acid | NaOH | 5 | 70.7 |
| Example 3 | Linolic acid | KOH | 5 | 84.0 |
| Example 4 | 10-Undecenoic acid | LiOH | 5 | 56.8 |
| Example 5 | 10-Undecenoic acid | NaOH | 5 | 68.1 |
| Example 6 | 10-Undecenoic acid | KOH | 5 | 65.3 |

Figure 2:
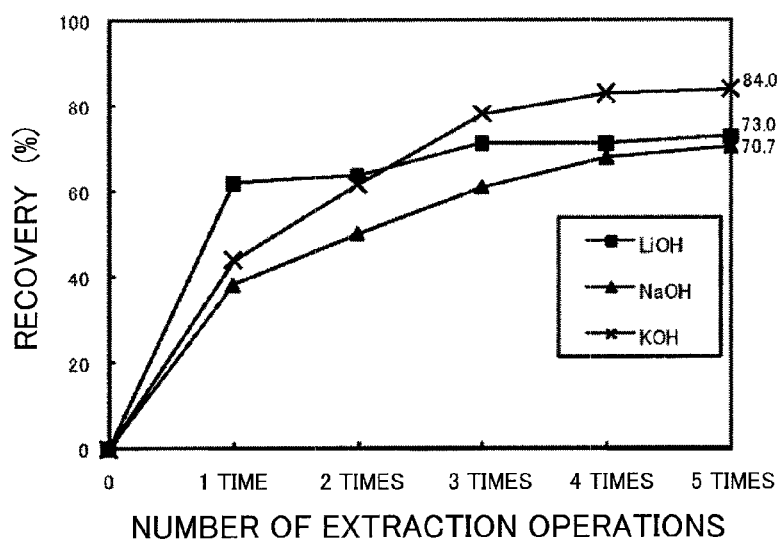
FIG. 2 is a diagram showing the relations between the number of extraction operations and the recovery.

FIG. 2 is a diagram showing the relations between the number of extraction operations and the recovery. The diagram shows the cases of Examples 1 to 3. It can be seen that when extraction is repeated, the recovery is enhanced.

Examples 7 and 8

Furthermore, 0.05 g of a lead chromate-containing PP resin powder which contained 0.1% by mass of hexavalent chromium was subjected to extraction according to the same procedure as that used in Examples 1 to 6. However, the number of extraction operations was set to 2 times. Furthermore, the recovery was calculated by the same procedure as that used in Examples 1 to 6. The results are presented in Table 3.

TABLE 3

|  | Organic fatty acid | Aqueous alkali solution | Number of extraction operations (times) | Recovery (%) |
|---|---|---|---|---|
| Example 7 | Linolic acid | NaOH | 2 | 76.8 |
| Example 8 | Linolic acid | KOH | 2 | 84.9 |

The effect that hexavalent chromium can be extracted from polymer materials with a high recovery, was confirmed by the Examples described above. In particular, when linolic acid was used as the fatty acid as in Examples 1 to 3 and Examples 7 and 8, an recovery as high as 70% or higher could be obtained. Furthermore, with a combination of linolic acid and an aqueous solution of potassium hydroxide according to Example 3, a particularly high recovery of 80% or higher could be obtained.

What is claimed is:

1. A method for extracting hexavalent chromium in a polymer material, the method comprising:
    adding a fatty acid to the polymer material and heating said fatty acid and polymer material to a temperature of up to 300° C. to prepare a heated uniform liquid sample; and
    cooling said heated uniform liquid sample and then adding water or an aqueous alkali solution to the cooled sample to form a treated sample, and extracting the hexavalent chromium contained in the treated sample by separating the treated sample into an oil layer and an aqueous layer, the hexavalent chromium being dissolved in the aqueous layer,
    wherein the polymer material is polyethylene (PE) resin or polypropylene (PP) resin, and the fatty acid has a carbon number of 11 or greater.

2. The method according to claim 1, comprising adding the aqueous alkali solution to the cooled sample, wherein the concentration of the aqueous alkali solution is from 0.1 mol/L to 1.0 mol/L.

3. The method according to claim 1, wherein the fatty acid has a melting point of 30° C. or lower and a boiling point of 200° C. or higher.

4. The method according to claim 1, wherein the fatty acid is 10-undecenoic acid, oleic acid, α-linolenic acid or linoleic acid.

5. The method according to claim 1, comprising adding the aqueous alkali solution to the cooled sample, wherein the aqueous alkali solution is an aqueous solution of LiOH, NaOH, or KOH.

6. The method according to claim 1, wherein the polymer material is polyethylene (PE) resin.

7. The method according to claim 1, wherein the polymer material is polypropylene (PP) resin.

8. The method according to claim 1, wherein the fatty acid is linoleic acid.

9. The method according to claim 8, comprising adding the aqueous alkali solution to the cooled sample, wherein the aqueous alkali solution is an aqueous solution of KOH.

10. The method according to claim 9, wherein the polymer material is polyethylene (PE) resin.

11. The method according to claim 9, wherein the polymer material is polypropylene (PP) resin.

12. The method according to claim 1, further comprising adding water or an aqueous alkali solution to the separated oil layer to form a mixture, and extracting hexavalent chromium contained in the separated oil layer by separating the mixture into an oil layer and an aqueous layer, the hexavalent chromium being dissolved in the aqueous layer.

13. The method according to claim 1, comprising heating said fatty acid and polymer material to a temperature of 170° C. or higher to prepare the heated uniform liquid sample.

14. The method according to claim 1, comprising cooling said heated uniform liquid sample to 90° C. or lower and then adding water or an aqueous alkali solution to the cooled sample to form the treated sample.

15. The method according to claim 1, wherein the polymer material is subjected to a pulverization treatment to finely divide the polymer material prior to the addition of the fatty acid.

16. The method according to claim 1, comprising adding the aqueous alkali solution to the cooled sample, wherein the aqueous alkali solution is an aqueous solution of KOH.

* * * * *